United States Patent
Lancieux et al.

(10) Patent No.: US 9,072,571 B2
(45) Date of Patent: Jul. 7, 2015

(54) HANDPIECE HAVING AN ELECTRICAL CONNECTION MEANS

(75) Inventors: Cédric Lancieux, Chabeuil (FR); Hervé Richard, Notre Dame de Bellecombe (FR)

(73) Assignee: ANTHOGYR, Sallanches (FR)

( * ) Notice: Subject to any disclaimer, the term of this patent is extended or adjusted under 35 U.S.C. 154(b) by 48 days.

(21) Appl. No.: 13/388,481

(22) PCT Filed: Jul. 30, 2010

(86) PCT No.: PCT/IB2010/053478
§ 371 (c)(1),
(2), (4) Date: Feb. 2, 2012

(87) PCT Pub. No.: WO2011/015980
PCT Pub. Date: Feb. 10, 2011

(65) Prior Publication Data
US 2012/0129124 A1    May 24, 2012

(30) Foreign Application Priority Data
Aug. 7, 2009 (FR) ........................... 09 55590

(51) Int. Cl.
*A61C 1/00* (2006.01)
*A61C 1/18* (2006.01)
*A61C 1/08* (2006.01)

(52) U.S. Cl.
CPC ............... *A61C 1/185* (2013.01); *A61C 1/088* (2013.01)

(58) Field of Classification Search
CPC ............ A61C 1/18; A61C 1/052; A61C 1/05; A61C 1/088; A61C 1/08; A61C 1/12; A61C 1/10; A61C 1/06; A61C 17/0202; A61C 17/005; A61C 19/004; A61C 1/07; A61C 1/141; A61C 1/145; A61C 1/147; A61C 1/185; A61C 1/186; A61C 1/188
USPC .................. 433/29, 82, 114, 126, 131, 105; 439/247, 252, 254, 255, 259, 700, 824
See application file for complete search history.

(56) References Cited

U.S. PATENT DOCUMENTS

| | | | |
|---|---|---|---|
| 4,521,189 A | 6/1985 | Lares | |
| 4,720,266 A * | 1/1988 | Leonard et al. | 433/126 |
| 5,501,596 A * | 3/1996 | Bailey | 433/86 |
| 5,641,315 A * | 6/1997 | Swart et al. | 439/824 |
| 7,179,087 B2 * | 2/2007 | Kuhn | 433/126 |
| 7,914,315 B2 * | 3/2011 | Kuhn et al. | 439/345 |

FOREIGN PATENT DOCUMENTS

| | | |
|---|---|---|
| FR | 2445134 A1 | 7/1980 |
| FR | 2579448 A1 | 10/1986 |

(Continued)

*Primary Examiner* — Yogesh Patel
(74) *Attorney, Agent, or Firm* — William H. Eilberg

(57) ABSTRACT

A dental handpiece (1) includes a head (2) suitable for driving a tool, a body (3) having a proximal section (4) extending in a longitudinal direction (I-I) and intended to be connected, by a proximal end surface (5), to a distal surface of a drive motor, an indexing device (8) suitable for rotatably positioning the body (3) of the dental handpiece (1) about the longitudinal direction (I-I) relative to the drive motor, an electric device (9) for lighting the working area of the tool, and a device (10) for supplying electric power to the electric lighting device (9). The indexing device (8) is retractable or set back from the proximal end surface (5), and the electric supply device (10) includes a retractable electrical connection device (11).

14 Claims, 12 Drawing Sheets

(56) References Cited

FOREIGN PATENT DOCUMENTS

| | | | |
|---|---|---|---|
| FR | 2592299 | A1 | 7/1987 |
| FR | 2673369 | A1 | 9/1992 |
| FR | 2709658 | A1 | 3/1995 |
| GB | 2188239 | A | 9/1987 |

\* cited by examiner

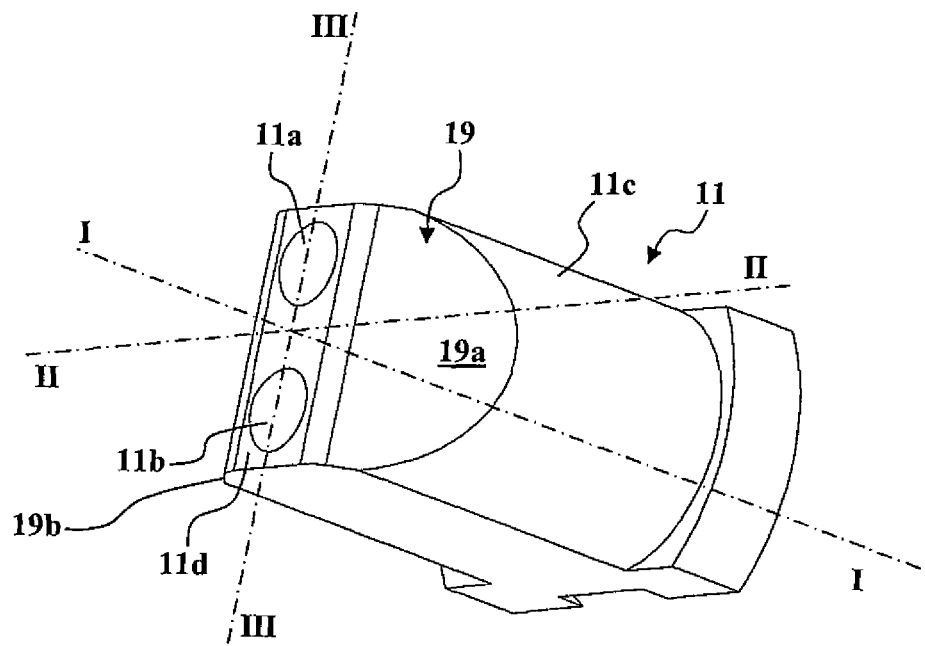
FIG. 6
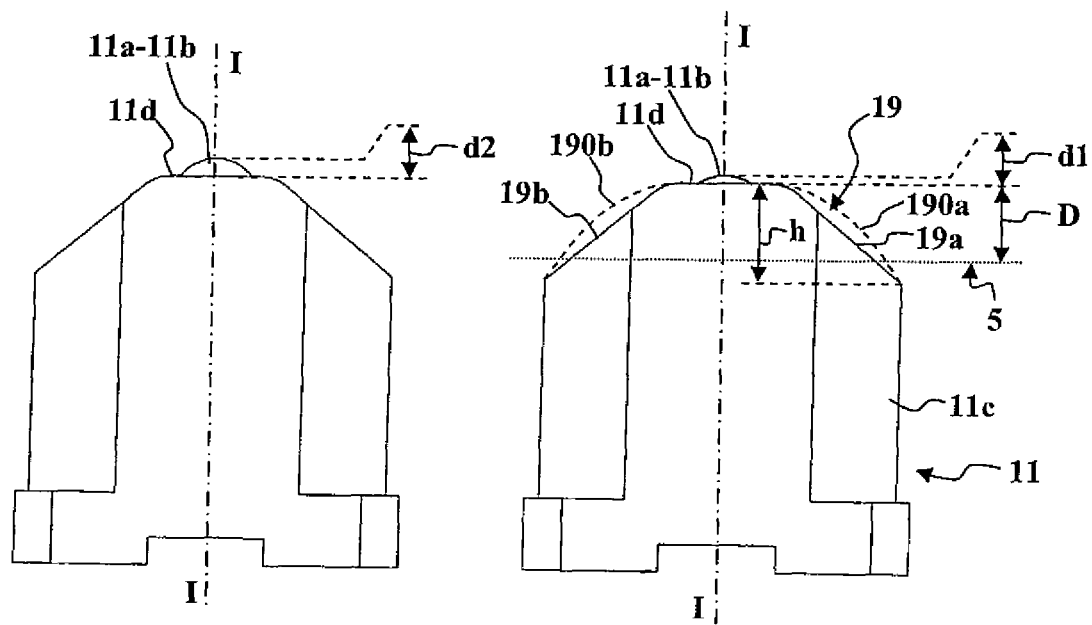
FIG. 8  FIG. 7

HANDPIECE HAVING AN ELECTRICAL CONNECTION MEANS

TECHNICAL FIELD OF THE INVENTION

The present invention relates to the field of surgical handpieces, and relates more particularly to a dental handpiece.

In an operation in the mouth of a patient, it is important for the practitioner to have a good view of what he or she is doing. For this, dental handpieces with electric means for lighting the working area are known. In the current embodiment, the handpiece comprises:
- a head suitable for driving a tool,
- a body with proximal section extending in a longitudinal direction and intended to be connected by a proximal end face to a distal face of a drive motor,
- indexing means in the form of a protruding snug, suitable for immobilizing the body of the dental handpiece in a defined angular position about the longitudinal direction relative to the drive motor,
- electric means for lighting the working area,
- electrical energy transfer means for transferring the electrical energy from the proximal end face to the electric lighting means, comprising electrical connection means.

The electric lighting means, borne by the handpiece, light the working area of the tool and are supplied with electrical energy by electrical energy conduction means passing axially through the drive motor to which the electrical energy transfer means in the dental handpiece are connected when the proximal end face of the dental handpiece is coupled to the distal face of the drive motor.

As described in document FR 2 673 369, the connection means are protruding and extend beyond the proximal end face of the handpiece body.

In order to be able to complete the operations begun in the mouth of the patient when the drive motor fails, practitioners usually retain their old drive motor or a less costly drive motor. More often than not, such motors do not have electrical energy conduction means on their distal face. These drive motors are commonly called "no-light" motors.

The presence of the indexing means and of electrical connection means extending from the proximal end face of the handpiece does, however, prevent the dental handpiece from being coupled to the distal face of a "no-light" drive motor.

The practitioner is then obliged to use a different dental handpiece, compatible with the "no-light" motor.

When the replacement "no-light" motor is the old drive motor that the practitioner used to use, the practitioner then has to be careful to retain the corresponding dental handpiece in order to reuse it in the event of failure of the drive motor of the dental handpiece with lighting means. Also, the practitioner must then use different tools to which he is no longer accustomed and which may not be suitable for the current operations in the mouth of the patient.

The document EP 0 181 669 describes a dental handpiece consisting of a head and a body that can be separated. Electrical connection output plugs permanently protrude from the proximal end face of the body and prevent the dental handpiece from being coupled to the distal face of a "no-light" drive motor.

The document FR 2 579 448 describes a dental handpiece provided, on the proximal end face of its body, with annular tracks which avoid the need for recourse to indexing means between the dental handpiece and the drive motor.

SUMMARY OF THE INVENTION

One issue proposed by the invention is to design a dental handpiece with lighting means which can be coupled for its drive to a "no-light" motor.

To achieve this and other aims, the invention proposes a dental handpiece comprising:
- a head suitable for driving a tool,
- a body with proximal section extending in a longitudinal direction and intended to be connected by a proximal end face to a distal face of a drive motor,
- indexing means, suitable for immobilizing the body of the dental handpiece in a defined angular position about the longitudinal direction relative to the drive motor,
- electric means for lighting the working area,
- electrical energy transfer means for transferring the electrical energy from the proximal end face to the electric lighting means, comprising electrical connection means, in which:
- the indexing means are retractable or set back relative to the proximal end face,
- the electrical connection means, comprising at least one contact terminal, can be displaced in the longitudinal direction between a retracted position in which the electrical connection means do not extend axially in the longitudinal direction beyond the proximal end face of the body, and a connection position in which the electrical connection means extend axially in the longitudinal direction beyond the proximal end face of the body,
- first elastic means permanently return the electrical connection means to the connection position.

The distal face of a "no-light" drive motor can thus receive the proximal end face of the dental handpiece for its coupling, without the indexing means and/or the electrical connection means opposing the relative axial convergence of the dental handpiece and of the drive motor. The electrical connection means, as well as the indexing means, when they are retractable, are in fact pushed back into the proximal section of the body of the dental handpiece upon coupling to the "no-light" drive motor whose distal face does not include any element intended to cooperate with the indexing means and the electrical connection means.

Also, when the dental handpiece is used with a drive motor provided with electrical energy conduction means suitable for cooperating with the electrical energy transfer means of the handpiece, the indexing means and the electrical connection means of the dental handpiece cooperate with the distal face of the drive motor without the user being required to perform any manipulation other than that of coupling the proximal end face of the dental handpiece to the distal face of the drive motor.

In a first embodiment, provision can be made for:
- the indexing means to comprise a retractable indexing snug borne by the handpiece, that can be displaced in the longitudinal direction between an indexing position, in which the indexing snug extends axially in the longitudinal direction beyond the proximal end face, and a retracted position, in which the indexing snug does not extend axially in the longitudinal direction beyond the proximal end face,
- second elastic means to permanently return the indexing snug to the indexing position,
- the indexing snug to be intended to cooperate with an indexing cavity borne by the distal face of the drive motor.

In a second embodiment, provision can be made for:
- the indexing means to comprise an indexing cavity borne by the proximal end face of the body of the dental handpiece,
- the indexing cavity to be intended to cooperate with a retractable indexing snug, borne by the distal face of the drive motor, which can be displaced in the longitudinal direction between an indexing position in which the indexing snug extends axially in the longitudinal direction beyond the distal face of the drive motor, and a retracted position in which the indexing snug does not extend axially in the longitudinal direction beyond the distal face of the drive motor,
- second elastic means to permanently return the indexing snug to the indexing position.

In these two embodiments, the indexing snug and the corresponding indexing cavity make it possible to immobilize the body of the dental handpiece in a defined angular position about the longitudinal direction relative to the drive motor, and do so in order to suitably position in a corresponding way the electrical energy transfer means of the dental handpiece and the electrical energy conduction means of the drive motor.

In a first variant of the first embodiment, provision can be made for the indexing snug and the electrical connection means to have:
- distinct respective radial positions away from the longitudinal axis of the proximal section of the handpiece body, and/or
- transversal sections of distinct respective forms, and/or
- transversal sections with one or more distinct respective dimensions, and/or
- distinct relative respective orientations about the longitudinal direction, chosen such that the electrical connection means cannot penetrate into the indexing cavity borne by the distal face of the drive motor when the handpiece and the drive motor are coaxial.

Any interference by the electrical connection means of the indexing of the dental handpiece relative to the drive motor about the longitudinal direction is thus avoided. In practice, when the electrical connection means cannot penetrate into the indexing cavity borne by the distal face of the drive motor, only the indexing snug can penetrate into the indexing cavity and reliably and safely determine the relative position of the dental handpiece and of the drive motor about the longitudinal direction.

According to a second variant of the first embodiment, provision can be made for:
- the electrical connection means to be able to penetrate into the indexing cavity borne by the distal face of the drive motor when the dental handpiece and the drive motor are coaxial,
- the electrical connection means to include escape means configured so that, when the electrical connection means have penetrated into the indexing cavity instead of the indexing snug, the electrical connection means can leave the indexing cavity when the body of the dental handpiece is displaced relative to the drive motor by a rotational movement about the longitudinal direction.

The electrical connection means do not thus block the relative rotation of the body of the dental handpiece relative to the drive motor in the longitudinal direction. The indexing is therefore achieved well by the indexing snug when the latter penetrates into the indexing cavity.

Furthermore, the escape of the electrical connection means from the indexing cavity does not disturb the practitioner in his or her usual approach to the coupling and indexing of the dental handpiece and of the drive motor.

Advantageously, provision can be made for:
- the electrical connection means to include a connection body having an end face bearing said at least one contact terminal,
- the escape means to comprise at least one ramp which extends in a direction substantially perpendicular to the longitudinal direction and substantially perpendicular to a radial direction,
- when the connection body is in the connection position, the ramp to link the end face of the connection body to the proximal end face of the handpiece body.

Preferably, the escape means may comprise two ramps extending away from one another along the direction substantially perpendicular to the longitudinal direction and substantially perpendicular to a radial direction.

There is thus an escape for the electrical connection means from the indexing cavity, when the latter have accidentally penetrated therein, in a simple and easy manner by a rotational movement about the longitudinal direction in either of the two possible directions of rotation.

Advantageously, the ramp or ramps may have a transversal profile substantially in the form of a circular arc or in the form of an oblique straight line.

Preferably, the first elastic means may exert a return force less than the return force exerted by the second elastic means.

The indexing means are thus guaranteed predominance when the dental handpiece is connected to the drive motor. In practice, the force of the user to connect the dental handpiece to the drive motor, in the event of an indexing defect affecting one relative to the other, will be exerted predominantly against the second elastic means returning the indexing snug to the indexing position.

Advantageously, the connection body may include a transversal section of non-circular form. Any risk of rotation thereof which could lead to a reversal of the polarities of the electrical energy is thus avoided.

Advantageously, in order to improve the electric contact between the dental handpiece and the drive motor, provision can be made for:
- said at least one contact terminal borne on the end face of the connection body to be able to be displaced in the longitudinal direction between a first position and a second position,
- in the second position, the contact terminal to extend beyond the end face of the connection body by an extension that is greater than in the first position,
- third elastic means to permanently return said at least one contact terminal to the second position.

According to another aspect, the invention aims to enable a dental handpiece with electric lighting means to be coupled to a drive motor that has, on its distal face, an incandescent lamp.

The practitioner is thus able to re-use an old motor with incandescent lamp as a repair or to change handpiece.

To achieve this aim, among other things, the invention proposes an adaptation kit comprising a dental handpiece as defined above and comprising an electrically-, mechanically- and geometrically-compatible coupling device to replace an incandescent lamp borne by the drive motor, with a view to tapping the power supply current and voltage provided for said incandescent lamp in order to conduct them to the electrical connection means of said handpiece.

In the adaptation kit according to the invention, a coupling device such as those described in the document FR 2 673 369 can be used.

Preferably, provision can be made for:

the coupling device to have at least one power supply terminal intended to come into contact with said at least one contact terminal of the electrical connection means, said at least one power supply terminal of the coupling device to be situated substantially in the hollow of a concave end face of the coupling device.

The concave end face of the coupling device makes it possible to guide the contact terminal of the electrical connection means toward the power supply terminal and do so in order to make it easier for them to be brought together and held together.

Advantageously, provision can be made for the coupling device to include at least one fuse providing protection against overvoltages or overcurrents. The practitioner and the patient are thus protected from any electrical defect of the handpiece and from any electrical defect of the drive motor.

Other objects, features and advantages of the present invention will become apparent from the following description of particular embodiments, given in relation to the appended figures, in which:

FIG. 6 is a perspective view of the electrical connection means of the dental handpiece of FIGS. 1 to 5;

FIG. 7 is a side view of the electrical connection means of FIG. 6;

FIG. 8 is another side view of the electrical connection means of FIG. 6;

DESCRIPTION OF THE PREFERRED EMBODIMENTS

Figure 1:
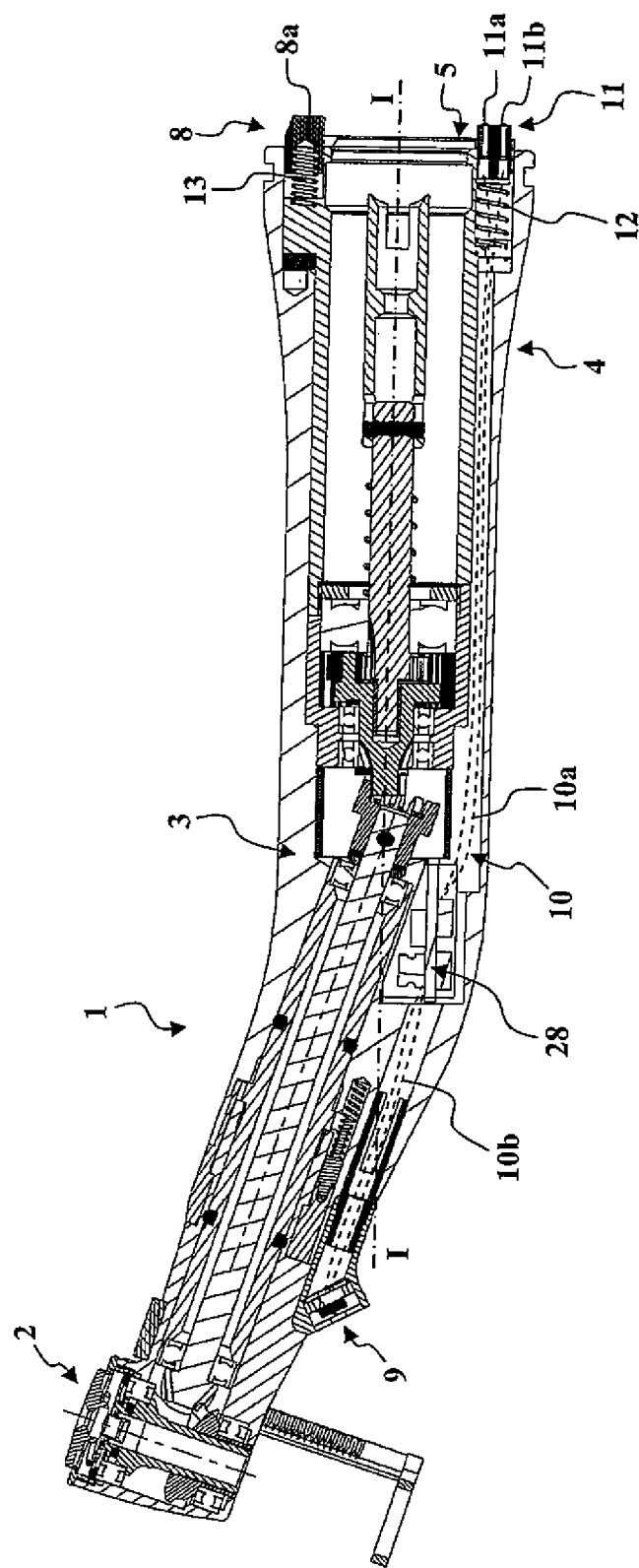
FIG. 1 is a cross-sectional view of the second variant of a first embodiment of the dental handpiece according to the invention.

FIGS. 1 to 5 represent a dental handpiece according to a second variant of a first embodiment of the invention.

In these figures, the dental handpiece 1 comprises:

a head 2 suitable for driving a tool (not represented), a body 3 with proximal section 4 extending in a longitudinal direction I-I and intended to be connected by a proximal end face 5 to a distal face 6 of a drive motor 7 (FIGS. 4 and 5), indexing means 8, adapted to immobilize the body 3 of the dental handpiece 1 in a defined angular position about the longitudinal direction I-I relative to the drive motor 7, electric lighting means 9 for lighting the working area of the tool, electrical energy transfer means 10 for transferring the electrical energy from the proximal end face to the electric lighting means 9.

The indexing means 8 can be retracted relative to the proximal end face 5.

More particularly, the indexing means 8 comprise a retractable indexing snug 8a borne by the dental handpiece 1, that can be moved in a longitudinal direction I-I between an indexing position (FIGS. 1 and 3) in which the indexing snug 8a extends axially in the longitudinal direction I-I beyond the proximal end face 5, and a retracted position (FIG. 2), in which the indexing snug 8a does not extend axially in the longitudinal direction I-I beyond the proximal end face 5. The indexing means 8 can thus be retracted into the proximal section 4 of the dental handpiece 1.

The electrical energy transfer means 10 comprise electrical connection means 11, comprising two contact terminals 11a and 11b, that can be displaced in the longitudinal direction I-I between a retracted position (FIG. 2) in which the electrical connection means 11 do not extend axially in the longitudinal direction I-I beyond the proximal end face 5 of the body 3, and a connection position (FIGS. 1 and 3) in which the electrical connection means 11 extend axially in the longitudinal direction I-I beyond the proximal end face 5 of the body 3.

First elastic means 12 permanently return the electrical connection means 11 to the connection position, whereas second elastic means 13 permanently return the indexing means 8 to the indexing position.

Figure 2:
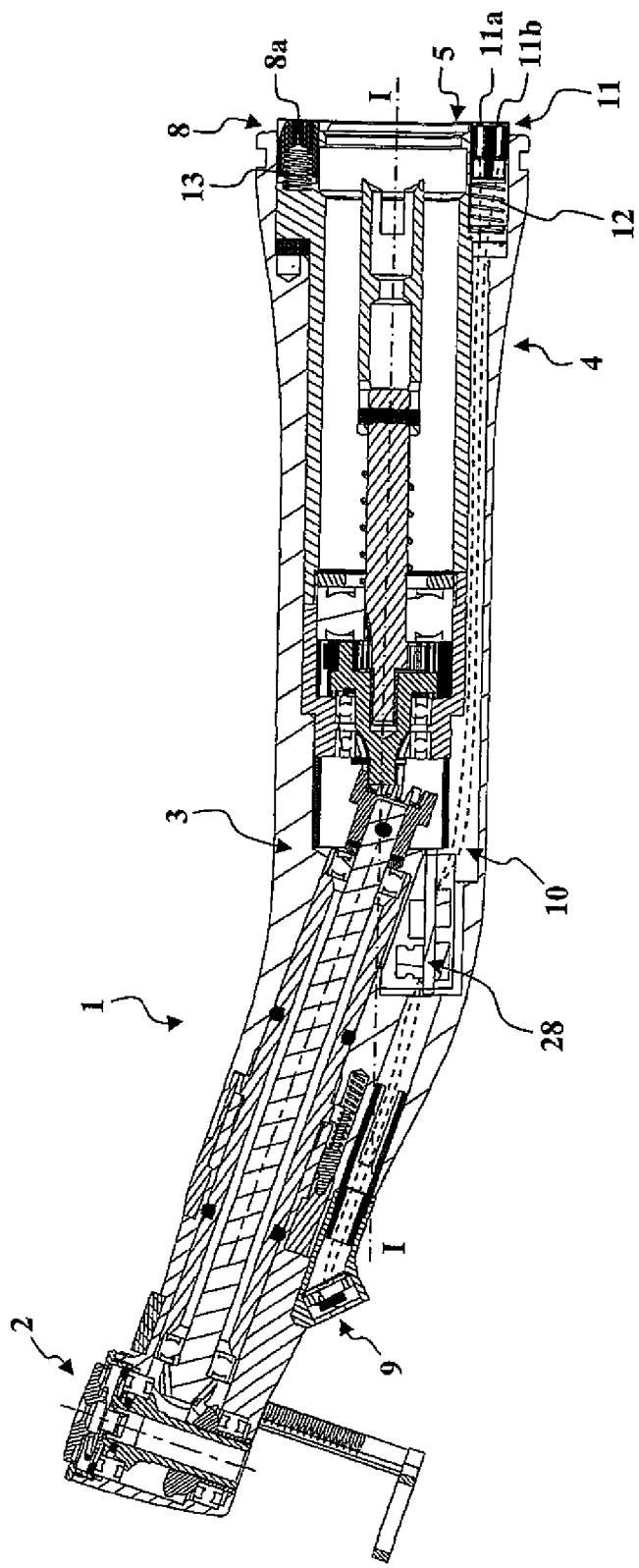
FIG. 2 is another cross-sectional view of the second variant of a first embodiment of the dental handpiece according to the invention.
Figure 3:
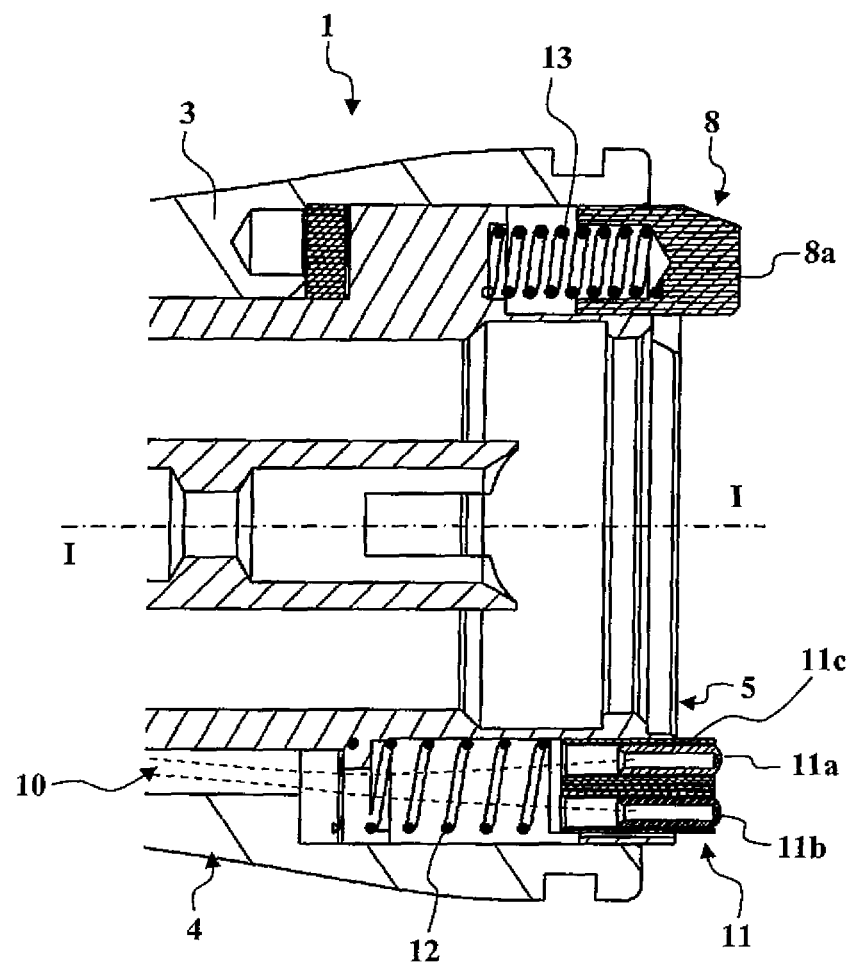
FIG. 3 is a detail view of FIG. 1.
Figure 4:
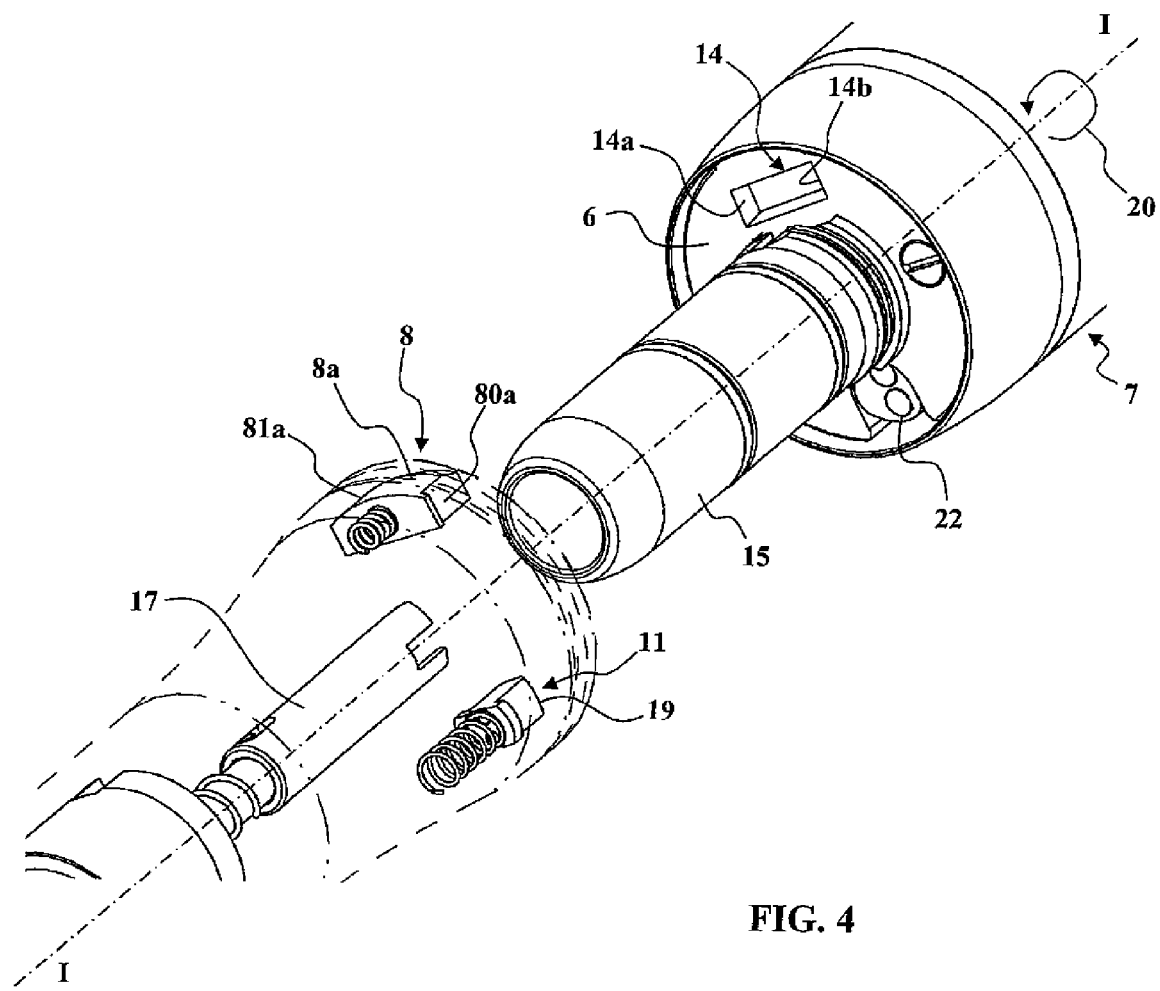
FIG. 4 is a perspective view illustrating the coupling of the dental handpiece of FIGS. 1 to 3 to a drive motor.
Figure 5:
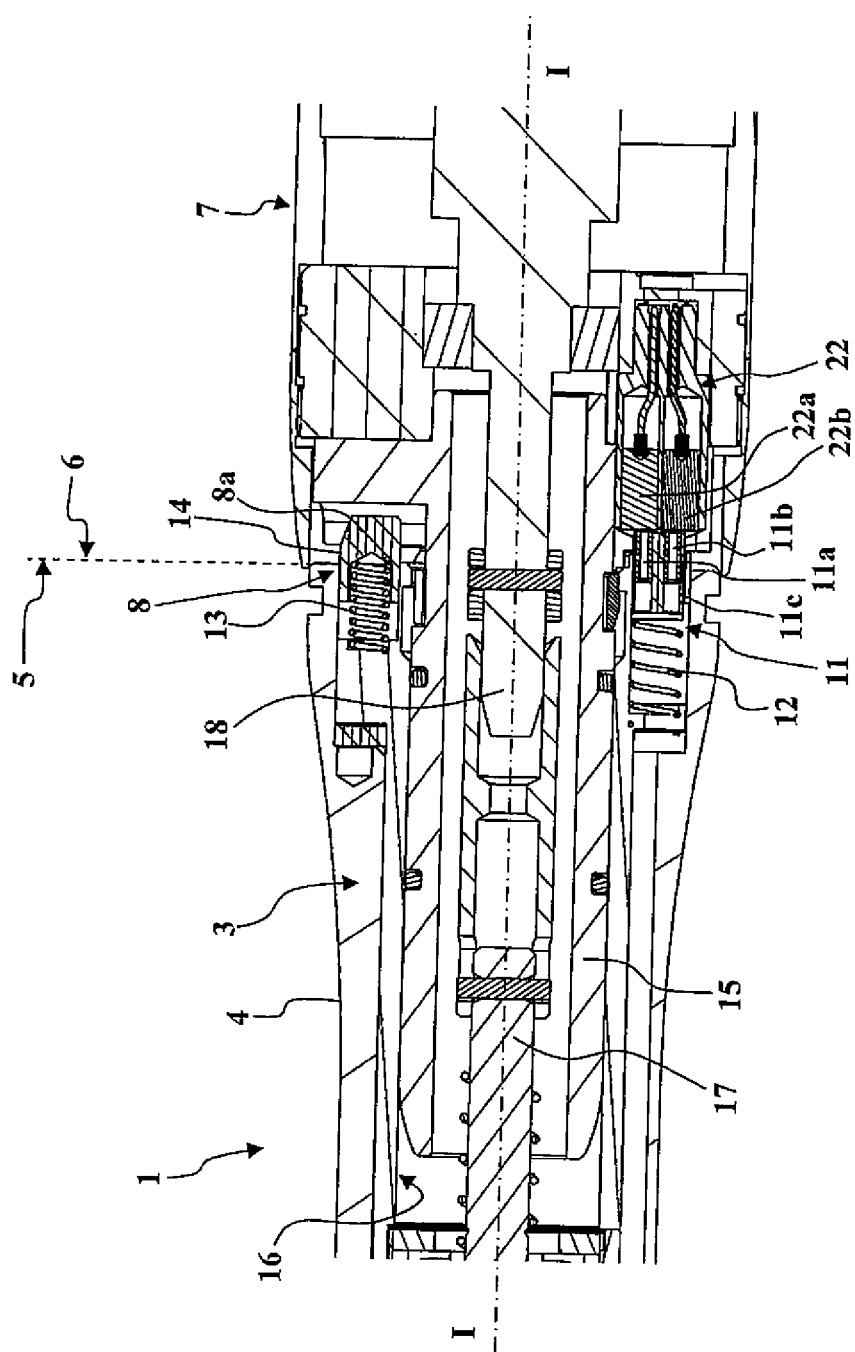
FIG. 5 is a cross-sectional view of the dental handpiece of FIGS. 1 to 4 coupled to a drive motor.

The connection of the dental handpiece 1 of FIGS. 1 to 3 to a drive motor 7 is illustrated in FIGS. 4 and 5. The drive motor 7 includes an indexing cavity 14 borne by the distal face 6, and intended to cooperate with the indexing snug 8a to position the body 3 of the dental handpiece 1 in a predetermined angular position about the longitudinal direction I-I relative to the drive motor 7.

For this, the indexing cavity 14 has two lateral facets 14a and 14b perpendicular to the distal face 6 (which is itself perpendicular to the longitudinal direction I-I). The indexing snug 8a itself has two lateral facets 80a and 81a perpendicular to the proximal end face 5, intended to bear against the lateral facets 14a and 14b when the indexing snug 8a is engaged with little play in the indexing cavity 14 (FIG. 5).

In a second embodiment of the dental handpiece according to the invention, not represented in the figures, but that can be understood by considering the same FIGS. 1 to 5, the indexing cavity 14 is made to be borne by the proximal end face 5 of the body 3 of the dental handpiece 1 and the indexing snug 8a is made to be borne by the drive motor 7. The indexing snug 8a can then be displaced in the longitudinal direction I-I between an indexing position in which it extends axially in the longitudinal direction I-I beyond the distal face 6 of the drive motor 7, and a retracted position in which it does not extend axially in the longitudinal direction I-I beyond the distal face 6 of the drive motor 7. The second elastic means 13 permanently return the indexing snug 8a to the indexing position. The indexing cavity 14, borne by the proximal end face 5 of the body 3 of the dental handpiece constitutes indexing means 8 which are set back relative to the proximal end face 5.

In the second embodiment of the dental handpiece 1 according to the invention, the electrical connection means 11 are identical to those of the first embodiment illustrated in FIGS. 1 to 5.

In the first embodiment, when the practitioner wants to connect the dental handpiece 1 of FIGS. 1 to 3 to a so-called "no-light" drive motor, that is to say, a drive motor with a perfectly smooth distal face without any cavities, the indexing snug 8a and the electrical connection means 11 are pushed back by the distal face of the drive motor into the proximal section 4 of the body 3. The indexing snug 8a and the electrical connection means 11 thus do not hamper the practitioner in coupling the dental handpiece 1 to a "no-light" drive motor. The practitioner can thus continue to use his or her dental handpiece 1 with electric lighting means 9, as well as the corresponding tools with which he was carrying out operations in the mouth of a patient before his or her drive motor 7 (powering the lighting means 9) failed.

Nor do the indexing snug 8a and the electrical connection means 11 hamper the practitioner in the case of a dental handpiece 1 according to the second embodiment: the indexing snug is retracted into the drive motor or penetrates into the indexing cavity 14 of the dental handpiece 1 whereas the electrical connection means 11 are pushed back into the retracted position by the distal face of the "no-light" drive motor.

When the dental handpiece 1 according to the first embodiment of the invention is coupled to the drive motor 7, the practitioner inserts a male centering coupling sleeve 15 borne by the drive motor 7 into a female cavity of the proximal section 4 of the body 3. The male centering coupling sleeve 15 is hollow in order to allow a transmission shaft 17 of the dental handpiece 1 to connect to a transmission shaft 18 of the drive motor 7 (FIGS. 4 and 5). When the indexing snug 8a is not exactly facing the indexing cavity 14, the practitioner exerts a relative rotational movement of the dental handpiece 1 relative to the drive motor 7 about the longitudinal direction I-I (movement illustrated by the arrow 20 in FIG. 4), until the indexing snug 8a is facing the indexing cavity 14 and penetrates therein, then immobilizing the relative rotational movement. During this rotational movement, the proximal end 5 and distal 6 faces are in contact or in immediate proximity. This indexing makes it possible to bring the electrical connection means 11 in line with the electrical energy conduction means of the drive motor 7.

During this indexing operation, it is essential that the electrical connection means 11, extending axially in the longitudinal direction I-I beyond the proximal end face 5, should not risk penetrating the indexing cavity 14, then producing an incorrect indexing of the dental handpiece 1 relative to the drive motor 7.

For this, according to a first variant of the first embodiment, it is advantageously possible to arrange for the electrical connection means 11 not to be able to penetrate into the indexing cavity 14 borne by the distal face 6 of the drive motor 7 when the dental handpiece 1 and the drive motor 7 are coaxial.

Figure 9:
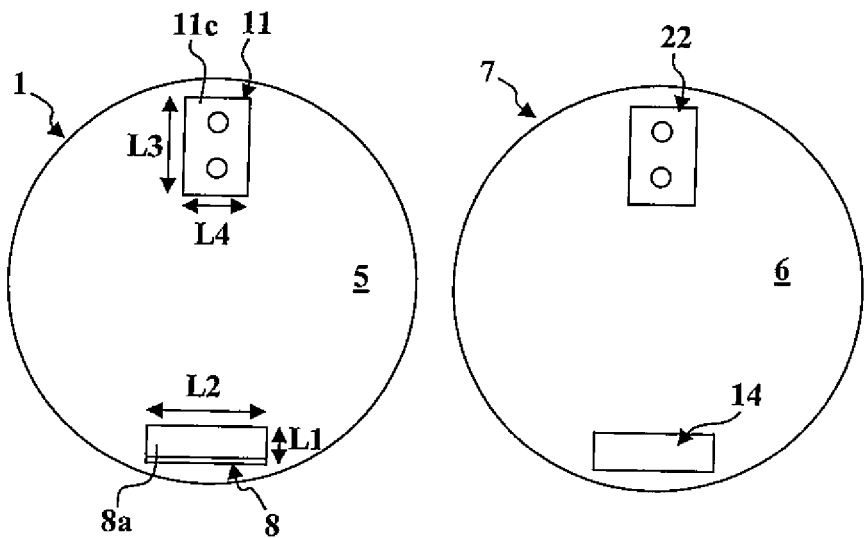
FIG. 9 is a schematic view of the proximal end face of the dental handpiece and of the distal face of a drive motor in a first variant of the first embodiment of the dental handpiece according to the invention.
Figure 10:
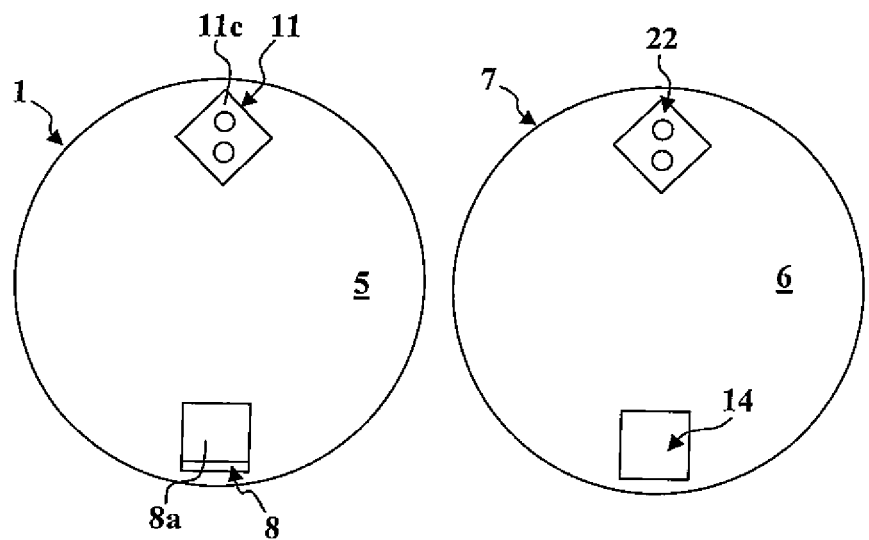
FIG. 10 is another schematic view of the proximal end face of the dental handpiece and of the distal face of a drive motor in a first variant of the first embodiment of the dental handpiece according to the invention.

To this end, provision can be made for the indexing snug 8a and the electrical connection means 11 to have:
  distinct respective radial positions away from the longitudinal axis of the body of the dental handpiece (FIG. 12), and/or
  transversal sections of distinct respective forms (FIG. 11), and/or
  transversal sections with one or more distinct respective dimensions (FIG. 9), and/or
  distinct relative respective orientations (FIG. 10).

FIGS. 9 to 12 are schematic representations of the proximal end face 5 of the dental handpiece 1 and of the distal face 6 of the drive motor 7 corresponding to these different possibilities.

In FIG. 9, the indexing snug 8a has a transversal section form of the same type as the electrical connection means 11, namely a rectangular form. The dimensions (lengths L1 and L2) of the transversal section of the indexing snug 8a differ however from the dimensions (lengths L3 and L4) of the transversal section of the electrical connection means 11, so that the electrical connection means 11 cannot penetrate into the indexing cavity 14 borne by the distal face 6 of the drive motor 7 when the dental handpiece 1 and the drive motor 7 are coaxial.

In FIG. 10, the indexing snug 8a and the electrical connection means 11 have transversal sections of the same type (square) and of the same dimensions. However, the relative respective orientations of the transversal sections of the indexing snug 8a and of the electrical connection means 11 are chosen such that the electrical connection means 11 cannot penetrate into the indexing cavity 14 borne by the distal face 6 of the drive motor 7 when the dental handpiece 1 and the drive motor 7 are coaxial.

Figure 11:
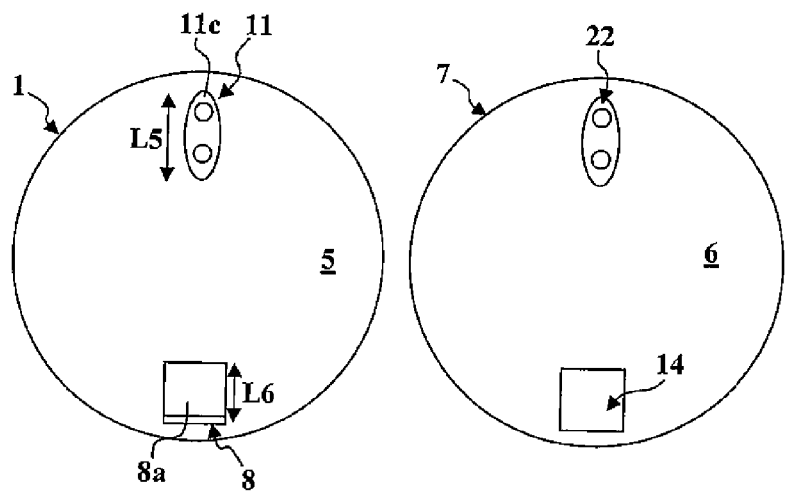
FIG. 11 is another schematic view of the proximal end face of the dental handpiece and of the distal face of a drive motor in a first variant of the first embodiment of the dental handpiece according to the invention.

In FIG. 11, the indexing snug 8a has a transversal section of square form whereas the electrical connection means 11 have a section in ellipsoid form. The ellipsoid form of the transversal section of the electrical connection means 11 has a major axis of length L5 greater than the length L6 of a side of the transversal section of the indexing snug 8a. The electrical connection means 11 thus cannot penetrate into the indexing cavity 14 borne by the distal face 6 of the drive motor 7 when the dental handpiece 1 and the drive motor 7 are coaxial.

Figure 12:
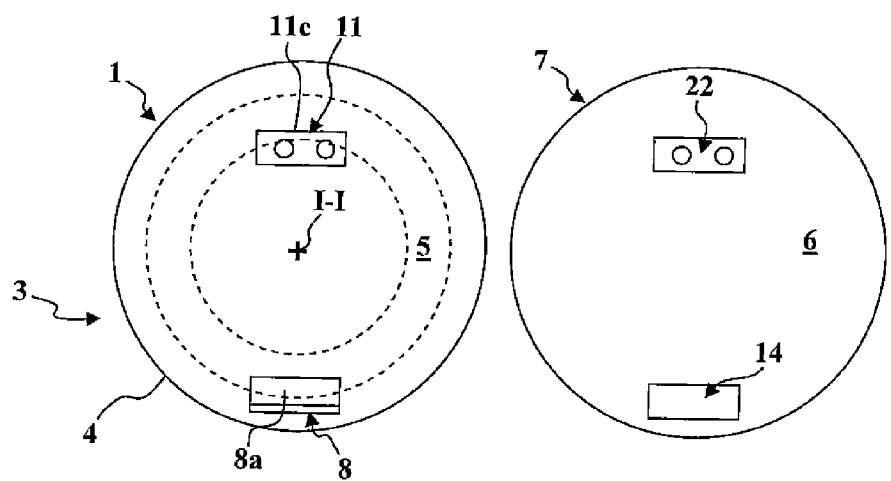
FIG. 12 is another schematic view of the proximal end face of the dental handpiece and of the distal face of a drive motor in a first variant of the first embodiment of the dental handpiece according to the invention.

In FIG. 12, the indexing snug 8a and the electrical connection means 11 have transversal sections of the same form (rectangular), of the same dimensions and with the same orientation. As represented with the broken line concentric circles, the indexing snug 8a and the electrical connection means 11 occupy distinct respective radial positions away from the longitudinal axis I-I of the proximal section 4 of the body 3 of the dental handpiece 1. As a result, the electrical connection means 11 cannot penetrate into the indexing cavity 14 borne by the distal face 6 of the drive motor 7 when the dental handpiece 1 and the drive motor 7 are coaxial.

In the case of the second variant of the first embodiment of the invention, it can be seen more particularly in FIG. 4 that the electrical connection means 11 can penetrate into the indexing cavity 14 borne by the distal face 6 of the drive motor 7 when the dental handpiece 1 and the drive motor 7 are coaxial. This is because the indexing snug 8a and the electrical connection means 11 have radial positions away from the longitudinal axis I-I that are diametrically opposite and the electrical connection means 11 have a transversal section of a form and dimensions that are smaller than those of the indexing snug 8a.

There are then proposed, so as not to disturb the indexing operations by the electrical connection means 11, escape means 19. The escape means 19 are ramps configured in such a way that, when the electrical connection means 11 have penetrated into the indexing cavity 14 instead of the indexing snug 8a, the electrical connection means 11 are pushed back axially and can leave the indexing cavity 14 when the body 3 of the dental handpiece 1 is displaced relative to the drive motor 7 by a rotational movement about the longitudinal direction I-I (illustrated by the arrow 20). The escape means 19 thus act, for the electrical connection means to escape from the indexing cavity 14, in a way that is compatible with the movement applied by the practitioner in the indexing operation.

The escape means 19 are better understood using FIGS. 6 to 8 in which the electrical connection means 11 comprise a connection body 11c with end face 11d bearing the contact terminals 11a and 11b. The escape means 19 comprise two ramps 19a and 19b extending away from one another in a direction II-II substantially perpendicular to the longitudinal direction I-I and substantially perpendicular to a radial direction III-III. As illustrated in FIG. 7, when the connection body 11c is in the connection position, the end face 11d extends beyond the proximal end face 5 (schematically represented by a broken line), by an extension D less than or equal to the height h of the ramps 19a and 19b. Thus, when the connection body 11c is in the connection position, the ramps 19a and 19b link the end face 11d of the connection body 11c to the proximal end face 5 of the body 3 of the handpiece.

It is specified that a single ramp 19a or 19b could suffice to guarantee the escape of the electrical connection means 11 from the indexing cavity 14. Nevertheless, the presence of the two ramps 19a and 19b enables the electrical connection means 11 to escape from the indexing cavity 14 regardless of the relative direction of rotation between the dental handpiece 1 and the drive motor 7 about the longitudinal direction I-I.

In FIGS. 6 to 8, the ramps 19a and 19b have a straight oblique transversal profile. They can, however, have a different transversal profile, for example in the form of a circular arc as illustrated by the broken lines 190a and 190b.

Again, in order to disrupt the indexing operation as little as possible by the presence of the electrical connection means 11 extending beyond the proximal end face 5, provision is advantageously made for the first elastic means 12 to exert a return force less than the return force exerted by the second elastic means 13. The indexing snug 8a is therefore predominant for performing the indexing operation, the electrical connection means 11 offering a lesser resistance to the practitioner when he or she couples the dental handpiece 1 to the drive motor 7 by the proximal end face 5 and the distal face 6.

It can be seen more particularly in FIGS. 6 to 8 that the connection body 11c includes a transversal section of non-circular form. The connection body 11c is arranged to slide into a recess of corresponding transversal section. The connection body 11c can thus only slide into its recess without being able to turn about the longitudinal direction I-I. Any risk of reversal of the contact terminals 11a and 11b when they tap the electrical energy is thus avoided. This is important when the electric lighting means 9 require a power supply according to a defined polarity (such as for an LED for example).

In order to guarantee a good contact of the contact terminals 11a and 11b with the electrical energy conduction means of the drive motor 7, the contact terminals 11a and 11b can be displaced in the longitudinal direction I-I between a first position (FIG. 7) and a second position (FIG. 8). In the second position (FIG. 8), the contact terminal extends beyond the end face 11d of the connection body 11c by an extension d2 greater than an extension d1 in the first position. Third elastic means (not visible) permanently return the contact terminals 11a and 11b to the second position.

Figure 13:
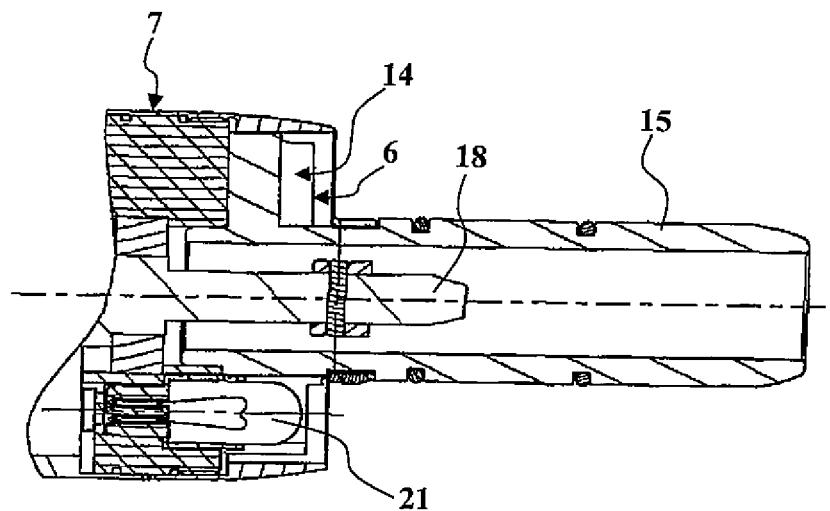
FIG. 13 is a partial cross-sectional view of a drive motor with incandescent lamp.

Very many practitioners have in their practices a drive motor 7 with incandescent lamp 21 as represented in FIG. 13. The incandescent lamp 21 is powered with electrical energy to produce a light energy. Such a drive motor is intended to receive a fiber optic dental handpiece such as that described in the document FR 2 551 651.

Figure 14:
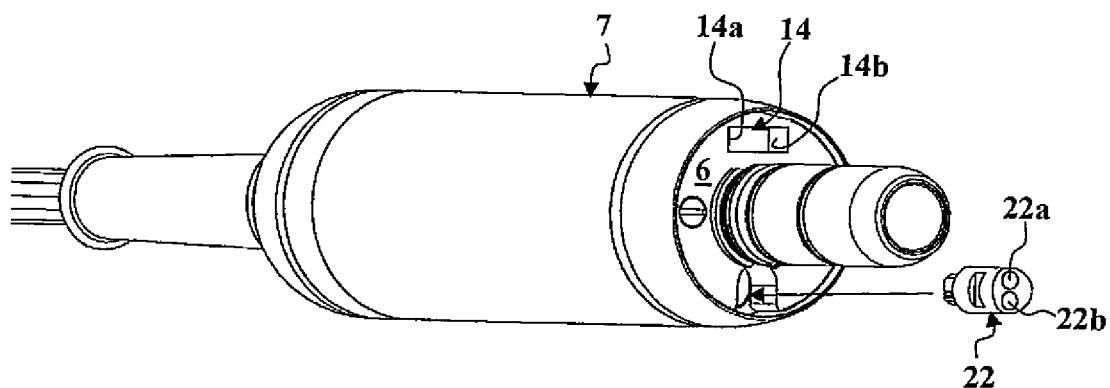
FIG. 14 is a perspective view of a drive motor with incandescent lamp to be replaced by a coupling device of an adaptation kit according to the invention.

To avoid the need for the practitioner to buy a new drive motor, it is advantageous to remove the incandescent lamp 21 and replace it with a coupling device 22, illustrated in FIG. 14, in order to tap the power supply currents and voltages provided for the incandescent lamp 21 in order to conduct them to the electrical connection means 11 of the dental handpiece 1. The coupling device 22 is electrically-, mechanically- and geometrically-compatible to replace the incandescent lamp 21 of the drive motor 7.

The coupling device 22 may be of the type of those described in the document FR 2 673 369. As illustrated in FIGS. 14 to 18, the coupling device 22 has two power supply terminals 22a and 22b intended to come into contact with the contact terminals 11a and 11b of the electrical connection means 11.

In the case of the use of a dental handpiece 1 according to the invention, with electrical connection means 11 that can be displaced in the longitudinal direction I-I, it is advantageous for the power supply terminals 22a and 22b to be situated substantially in the hollow of a concave end face 22c of the coupling device 22. The concavity of the concave end face 22c in fact has a tendency to bring the contact terminals 11a and 11b into line with the power supply terminals 22a and 22b in the event of a slight offset between the coupling device 22 and the electrical connection means 11.

Figure 17:
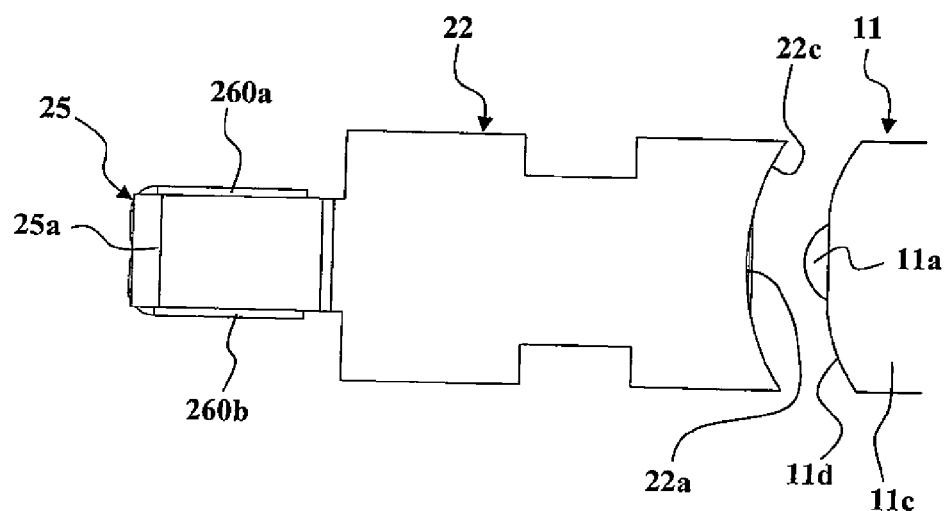
FIG. 17 is a side view of the coupling device of FIGS. 15 and 16.

In addition, and as illustrated in FIG. 17, it is advantageous to provide for the contact terminals 11a and 11b of the electrical connection means 11 to be situated substantially at the summit of a convex end face 11d. The concavity of the end face 22c and the convexity of the end face 11d are chosen to cooperate in order to relatively center the contact terminals 11a and 11b with the power supply terminals 22a and 22b. This can be obtained by the choice of concavity and convexity with corresponding radius of curvature.

Depending on the form of the socket of the incandescent lamp 21, a coupling device 22 having a suitable connection plug 25 can be chosen.

Figure 15:
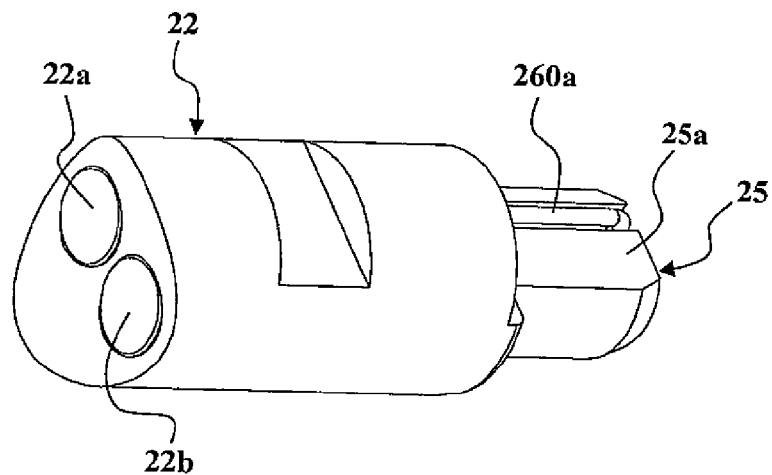
FIG. 15 is a perspective view of a first type of coupling device.
Figure 16:
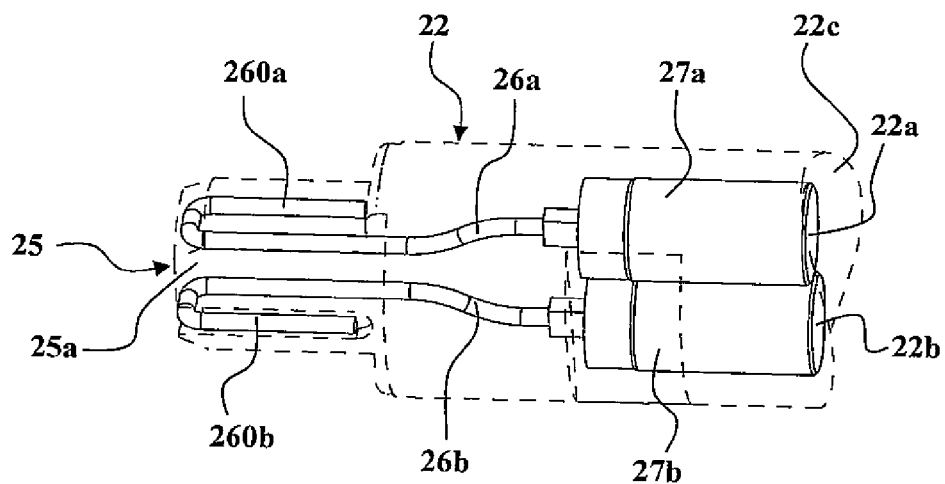
FIG. 16 is another perspective view of a first type of coupling device.

In the coupling device 22 of FIGS. 15 to 17, the connection plug 25 comprises a central pin 25a made of insulating material. Two conductors 26a and 26b, respectively linked to the power supply terminals 22a and 22b, pass through the coupling device 22 and are folded back by their respective free end 260a and 260b on either side of the central pin 25a.

Figure 18:
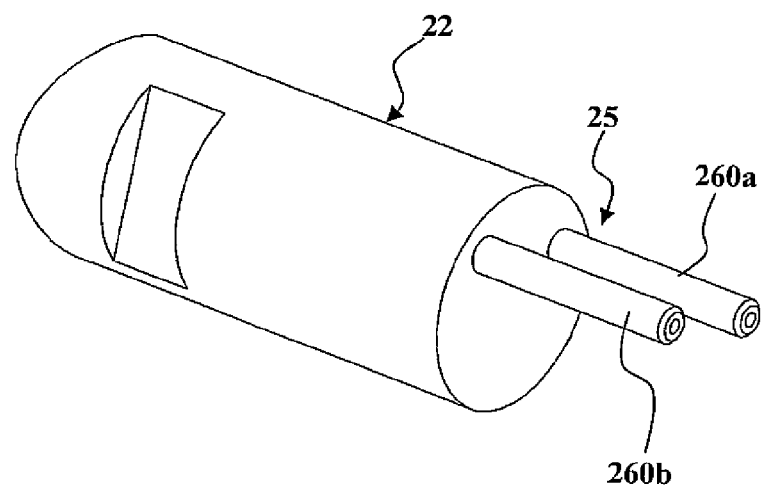
FIG. 18 is a perspective view of a second type of coupling device.

Another type of connection plug 25 is illustrated on the coupling device 22 of FIG. 18. In this figure, the free ends 260a and 260b of the conductors 26a and 26b extend longitudinally away from the coupling device 22 and are intended to be respectively plugged into two connection holes of the drive motor 7.

In order to protect the practitioner and the patient against overvoltages or overcurrents, each power supply terminal 22*a* and 22*b* of the coupling device 22 is connected in series with a fuse 27*a* and 27*b* (FIG. 16).

The polarities of the electrical energy supply of the incandescent lamp 21 of the drive motor 7 are rarely indicated, an incandescent lamp 21 not requiring any particular polarity. It is therefore not known what will be the polarity of the electrical energy tapped by the contact terminals 11*a* and 11*b* at the power supply terminals 22*a* and 22*b* of the coupling device 22. This may cause the electric lighting means 9 to be damaged or even destroyed, if said electric lighting means require a polarized electric supply (an LED for example).

A processing circuit 28 is therefore provided (FIG. 1) to which the electrical energy tapped by the contact terminals 11*a* and 11*b* is routed by a line 10*a*. The electric processing circuit 28 rectifies the voltage, for example by means of a diode rectifier bridge, which then makes it possible to supply the electric lighting means 9 with electrical energy with suitable polarity.

Figure 19:
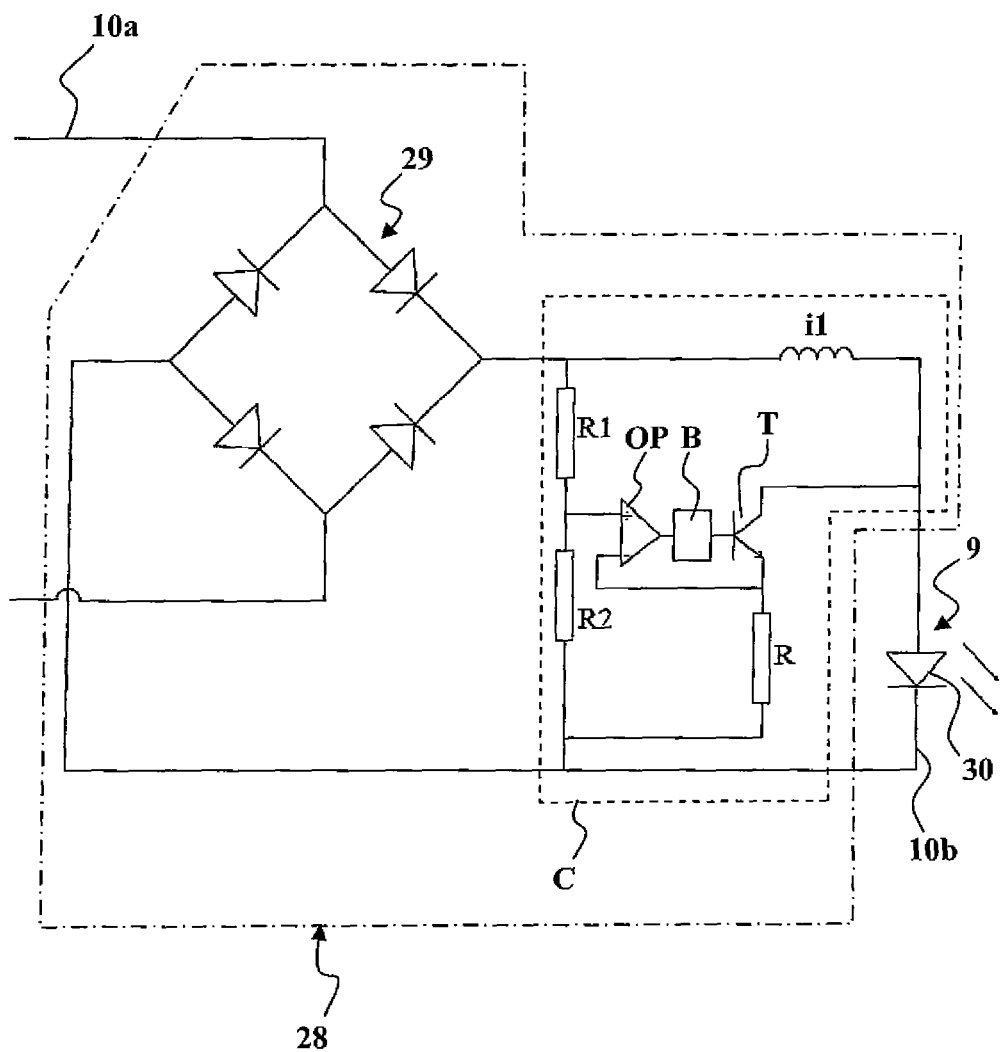
FIG. 19 is an example of an electric signal processing circuit which can be used in a dental handpiece according to the invention.

An example of an electric processing circuit 28 is illustrated in FIG. 19. In this figure, the electric processing circuit 28 comprises a diode bridge 29 for the rectification of the input voltage received on the line 10*a*.

In the case of the use of electric lighting means 9 by LED 30, it is also important to avoid having the LED 30 overheat. Now, the intensity of the electrical energy supplying an incandescent lamp (which will be tapped by the electrical connection means 11) is between approximately 300 mA and approximately 350 mA. Such an intensity is much too high and risks causing an excessive overheating of the LED 30 and causing its life to be significantly reduced.

To resolve this difficulty, it is advantageously possible to provide an intensity regulation circuit C, which makes it possible to supply the LED 30 with a regulated electric signal with an intensity of between approximately 30 mA and approximately 100 mA. Preferably, the regulated electric signal has an intensity of approximately 80 mA.

An exemplary embodiment of the intensity regulation circuit C is illustrated in FIG. 19. The circuit C is electrically connected between the output of the diode bridge 29 and an output line 10*b* which supplies the LED 30.

In this particular embodiment of the circuit C, an inductance i1 is connected in series with the LED 30 at the output of the diode bridge 29. An operational amplifier OP receives on its non-inverting input a set-point voltage set by a resistor bridge R1, R2 connected to the output of the diode bridge 29. A switching transistor T is connected in series with a resistor R to the terminals of the LED 30 and its base is controlled by a monostable trigger circuit B triggered by the output signal from the operational amplifier OP. The inverting input of the operational amplifier OP is connected to the connection between the resistor R and the emitter of the switching transistor T. The circuit C regulates the current in the LED 30 by chopping.

The intensity of the electric signal powering the LED 30 is adjusted by means of the value of the inductance i1.

The advantage of the electric processing circuit 28 illustrated in FIG. 19 is its great simplicity, its low cost, and its low consumption.

The electric processing circuit 28 of FIG. 19 makes it possible, by virtue of its intensity regulation circuit C, to regulate the intensity of the electrical energy which comes from most of the drive motors with incandescent lamps that are on the market, and thus makes it possible to reliably power a handpiece with LED.

The need for recourse to a complex and costly solution, such as that described in the document US 2007/0054232 which uses a multitude of means for detecting the characteristics of the light source of the handpiece and the characteristics of the electric signal from the drive motor, is thus avoided.

It will be noted that the intensity regulation means, comprising the circuit C, in themselves constitute an invention that is independent of the electrical connection means 11 described previously.

The present invention is not limited to the embodiments that have been explicitly described, but it includes the diverse variants and generalizations thereof contained within the scope of the following claims.

The invention claimed is:

1. A dental handpiece (1) comprising:
a head (2) suitable for driving a tool,
a body (3) with a proximal section (4) extending in a longitudinal direction (I-I) and intended to be connected by a proximal end face (5) to a distal face (6) of a drive motor (7),
indexing means (8), suitable for immobilizing the body (3) of the dental handpiece (1) in a defined angular position about the longitudinal direction (I-I) relative to the drive motor (7),
electric means (9) for lighting the working area,
electrical energy transfer means (10) for transferring electrical energy from the proximal end face (5) to the electric lighting means (9), comprising electrical connection means (11),
wherein:
the indexing means (8) are distinct from the electrical connection means and are retractable or set back relative to the proximal end face (5),
the electrical connection means (11) comprise a connection body (11*c*) bearing two contact terminals (11*a*, 11*b*), wherein said connection body (11*c*) can be displaced in the longitudinal direction (I-I) between a retracted position in which the electrical connection means (11) do not extend axially in the longitudinal direction (I-I) beyond the proximal end face (5) of the body (3), and a connection position in which the electrical connection means (11) extend axially in the longitudinal direction (I-I) beyond the proximal end face (5) of the body (3),
first elastic means (12) permanently exerting a force tending to return the connection body (11*c*) to the connection position,
wherein:
the indexing means (8) comprise an indexing cavity (14) borne by the proximal end face (5) of the body (3) of the dental handpiece (1),
the indexing cavity (14) is intended to cooperate with a retractable indexing snug (8*a*), borne by the distal face (6) of the drive motor (7), which can be displaced in the longitudinal direction (I-I) between an indexing position in which the indexing snug (8*a*) extends axially in the longitudinal direction (I-I) beyond the distal face (6) of the drive motor (7), and a retracted position in which the indexing snug (8*a*) does not extend axially in the longitudinal direction (I-I) beyond the distal face (6) of the drive motor (7),
second elastic means (13) permanently exerting a force tending to return the indexing snug (8*a*) to the indexing position.

2. The dental handpiece (1) as claimed in claim 1, wherein the first elastic means (12) exert a return force less than the return force exerted by the second elastic means (13).

3. The dental handpiece (1) as claimed in claim 1, wherein the connection body (11c) includes a transversal section of non-circular form.

4. A dental handpiece (1) comprising:
a head (2) suitable for driving a tool,
a body (3) with a proximal section (4) extending in a longitudinal direction (I-I) and intended to be connected by a proximal end face (5) to a distal face (6) of a drive motor (7),
indexing means (8), suitable for immobilizing the body (3) of the dental handpiece (1) in a defined angular position about the longitudinal direction (I-I) relative to the drive motor (7),
electric means (9) for lighting the working area,
electrical energy transfer means (10) for transferring electrical energy from the proximal end face (5) to the electric lighting means (9), comprising electrical connection means (11),
wherein:
the indexing means (8) are distinct from the electrical connection means and are retractable or set back relative to the proximal end face (5),
the electrical connection means (11) comprise a connection body (11c) bearing two contact terminals (11a, 11b), wherein said connection body (11c) can be displaced in the longitudinal direction (I-I) between a retracted position in which the electrical connection means (11) do not extend axially in the longitudinal direction (I-I) beyond the proximal end face (5) of the body (3), and a connection position in which the electrical connection means (11) extend axially in the longitudinal direction (I-I) beyond the proximal end face (5) of the body (3),
first elastic means (12) permanently exerting a force tending to return the connection body (11c) to the connection position,
wherein:
the indexing means (8) comprise a retractable indexing snug (8a) borne by the dental handpiece (1), that can be displaced in the longitudinal direction (I-I) between an indexing position, in which the indexing snug (8a) extends axially in the longitudinal direction (I-I) beyond the proximal end face (5), and a retracted position, in which the indexing snug (8a) does not extend axially in the longitudinal direction (I-I) beyond the proximal end face (5),
second elastic means (13) permanently exerting a force tending to return the indexing snug (8a) to the indexing position,
the indexing snug (8a) is intended to cooperate with an indexing cavity (14) borne by the distal face (6) of the drive motor (7).

5. The dental handpiece (1) as claimed in claim 4, wherein the indexing snug (8a) and the electrical connection means (11) have:
distinct respective radial positions away from the longitudinal axis (I-I) of the proximal section (4) of the body (3) of the dental handpiece (1),
and/or
transversal sections of distinct respective forms,
and/or
transversal sections with one or more distinct respective dimensions (L1-L6),
and/or
distinct relative respective orientations about the longitudinal direction,
chosen such that the electrical connection means (11) cannot penetrate into the indexing cavity (14) borne by the distal face (6) of the drive motor (7) when the dental handpiece (1) and the drive motor (7) are coaxial.

6. The dental handpiece (1) as claimed in claim 4, wherein:
the electrical connection means (11) can penetrate into the indexing cavity (14) borne by the distal face (6) of the drive motor (7) when the dental handpiece (1) and the drive motor (7) are coaxial,
the electrical connection means (11) include escape means (19) configured so that, when the electrical connection means (11) have penetrated into the indexing cavity (14) instead of the indexing snug (8a), the electrical connection means (11) can leave the indexing cavity (14) when the body (3) of the dental handpiece (1) is displaced relative to the drive motor (7) by a rotational movement (20) about the longitudinal direction (I-I).

7. The dental handpiece (1) as claimed in claim 6, wherein:
the connection body (11c) has an end face (11d) bearing said two contact terminals (11a, 11b),
the escape means (19) comprise at least one ramp (19a, 19b) which extends in a direction (II-II) substantially perpendicular to the longitudinal direction (I-I) and substantially perpendicular to a radial direction (III-III),
when the connection body (11c) is in the connection position, the ramp (19a, 19b) links the end face (11d) of the connection body (11c) to the proximal end face (5) of the body (3) of the dental handpiece (1).

8. The dental handpiece (1) as claimed in claim 7, wherein the escape means (19) comprise two ramps (19a, 19b) extending away from one another along the direction (II-II) substantially perpendicular to the longitudinal direction (I-I) and substantially perpendicular to a radial direction (III-III).

9. The dental handpiece (1) as claimed in claim 7, wherein the ramp or ramps (19a, 19b) have a transversal profile substantially in the form of a circular arc (190a, 190b) or in the form of an oblique straight line.

10. The dental handpiece (1) as claimed in claim 4, wherein the first elastic means (12) exert a return force less than the return force exerted by the second elastic means (13).

11. The dental handpiece (1) as claimed in claim 4, wherein the connection body (11c) includes a transversal section of non-circular form.

12. A dental handpiece (1) comprising:
a head (2) suitable for driving a tool,
a body (3) with a proximal section (4) extending in a longitudinal direction (I-I) and intended to be connected by a proximal end face (5) to a distal face (6) of a drive motor (7),
indexing means (8), suitable for immobilizing the body (3) of the dental handpiece (1) in a defined angular position about the longitudinal direction (I-I) relative to the drive motor (7),
electric means (9) for lighting the working area,
electrical energy transfer means (10) for transferring electrical energy from the proximal end face (5) to the electric lighting means (9), comprising electrical connection means (11),
wherein:
the indexing means (8) are distinct from the electrical connection means and are retractable or set back relative to the proximal end face (5),
the electrical connection means (11) comprise a connection body (11c) bearing two contact terminals (11a, 11b), wherein said connection body (11c) can be displaced in the longitudinal direction (I-I) between a retracted position in which the electrical connection means (11) do not extend axially in the longitudinal direction (I-I) beyond the proximal end face (5) of the body (3), and a connection position in which the electrical connection means (11) extend axially in the longitudinal direction (I-I) beyond the proximal end face (5) of the body (3), first elastic means (12) permanently exerting a force tending to return the connection body (11c) to the connection position, wherein the indexing means (8) comprise a retractable indexing snug (8a) borne by the dental handpiece (1), that can be displaced in the longitudinal direction (I-I) between an indexing position, in which the indexing snug (8a) extends axially in the longitudinal direction (I-I) beyond the proximal end face (5), and a retracted position, in which the indexing snug (8a) does not extend axially in the longitudinal direction (I-I) beyond the proximal end face (5), second elastic means (13) permanently exerting a force tending to return the indexing snug (8a) to the indexing position, wherein the indexing snug (8a) is intended to cooperate with an indexing cavity (14) borne by the distal face (6) of the drive motor (7), wherein the indexing snug (8a) and the electrical connection means (11) have:

distinct respective radial positions away from the longitudinal axis (I-I) of the proximal section (4) of the body (3) of the dental handpiece (1), and/or transversal sections of distinct respective forms, and/or transversal sections with one or more distinct respective dimensions (L1-L6), and/or distinct relative respective orientations about the longitudinal direction, chosen such that the electrical connection means (11) cannot penetrate into the indexing cavity (14) borne by the distal face (6) of the drive motor (7) when the dental handpiece (1) and the drive motor (7) are coaxial.

13. A dental handpiece (1) comprising:

a head (2) suitable for driving a tool, a body (3) with a proximal section (4) extending in a longitudinal direction (I-I) and intended to be connected by a proximal end face (5) to a distal face (6) of a drive motor (7), indexing means (8), suitable for immobilizing the body (3) of the dental handpiece (1) in a defined angular position about the longitudinal direction (I-I) relative to the drive motor (7), electric means (9) for lighting the working area, electrical energy transfer means (10) for transferring electrical energy from the proximal end face (5) to the electric lighting means (9), comprising electrical connection means (11), wherein:

the indexing means (8) are distinct from the electrical connection means and are retractable or set back relative to the proximal end face (5), the electrical connection means (11) comprise a connection body (11c) bearing two contact terminals (11a, 11b), wherein said connection body (11c) can be displaced in the longitudinal direction (I-I) between a retracted position in which the electrical connection means (11) do not extend axially in the longitudinal direction (I-I) beyond the proximal end face (5) of the body (3), and a connection position in which the electrical connection means (11) extend axially in the longitudinal direction (I-I) beyond the proximal end face (5) of the body (3), first elastic means (12) permanently exerting a force tending to return the connection body (11c) to the connection position, wherein the indexing means (8) comprise a retractable indexing snug (8a) borne by the dental handpiece (1), that can be displaced in the longitudinal direction (I-I) between an indexing position, in which the indexing snug (8a) extends axially in the longitudinal direction (I-I) beyond the proximal end face (5), and a retracted position, in which the indexing snug (8a) does not extend axially in the longitudinal direction (I-I) beyond the proximal end face (5), second elastic means (13) permanently exerting a force tending to return the indexing snug (8a) to the indexing position, wherein the indexing snug (8a) is intended to cooperate with an indexing cavity (14) borne by the distal face (6) of the drive motor (7), wherein the indexing snug (8a) and the electrical connection means (11) have:

transversal sections of distinct respective forms, and/or transversal sections with one or more distinct respective dimensions (L1-L6), and/or distinct relative respective orientations about the longitudinal direction, chosen such that the electrical connection means (11) cannot penetrate into the indexing cavity (14) borne by the distal face (6) of the drive motor (7) when the dental handpiece (1) and the drive motor (7) are coaxial.

14. A dental handpiece (1) comprising:

a head (2) suitable for driving a tool, a body (3) with a proximal section (4) extending in a longitudinal direction (I-I) and intended to be connected by a proximal end face (5) to a distal face (6) of a drive motor (7), indexing means (8), suitable for immobilizing the body (3) of the dental handpiece (1) in a defined angular position about the longitudinal direction (I-I) relative to the drive motor (7), electric means (9) for lighting the working area, electrical energy transfer means (10) for transferring electrical energy from the proximal end face (5) to the electric lighting means (9), comprising electrical connection means (11), wherein:

the indexing means (8) are distinct from the electrical connection means and are retractable or set back relative to the proximal end face (5), the electrical connection means (11) comprise a connection body (11c) bearing two contact terminals (11a, 11b), wherein said connection body (11c) can be displaced in the longitudinal direction (I-I) between a retracted position in which the electrical connection means (11) do not extend axially in the longitudinal direction (I-I) beyond the proximal end face (5) of the body (3), and a connection position in which the electrical connection means (11) extend axially in the longitudinal direction (I-I) beyond the proximal end face (5) of the body (3), first elastic means (12) permanently exerting a force tending to return the connection body (11*c*) to the connection position, wherein:

the indexing means (8) comprise an indexing cavity (14) borne by the proximal end face (5) of the body (3) of the dental handpiece (1), the indexing cavity (14) is intended to cooperate with a retractable indexing snug (8*a*), borne by the distal face (6) of the drive motor (7), which can be displaced in the longitudinal direction (I-I) between an indexing position in which the indexing snug (8*a*) extends axially in the longitudinal direction (I-I) beyond the distal face (6) of the drive motor (7), and a retracted position in which the indexing snug (8*a*) does not extend axially in the longitudinal direction (I-I) beyond the distal face (6) of the drive motor (7), second elastic means (13) permanently exerting a force tending to return the indexing snug (8*a*) to the indexing position, and wherein the first elastic means (12) exert a return force less than the return force exerted by the second elastic means (13).

\* \* \* \* \*